(12) United States Patent
Ahmed

(10) Patent No.: US 6,852,868 B2
(45) Date of Patent: *Feb. 8, 2005

(54) PROCESSES FOR THE PREPARATION OF 2-METHYLFURAN AND 2-METHYLTETRAHYDROFURAN

(75) Inventor: Irshad Ahmed, Mahwah, NJ (US)

(73) Assignee: Pure Energy Corporation, Paramus, NJ (US)

( * ) Notice: Subject to any disclaimer, the term of this patent is extended or adjusted under 35 U.S.C. 154(b) by 137 days.

This patent is subject to a terminal disclaimer.

(21) Appl. No.: 10/225,809

(22) Filed: Aug. 21, 2002

(65) Prior Publication Data

US 2003/0018205 A1 Jan. 23, 2003

Related U.S. Application Data

(63) Continuation of application No. 09/697,240, filed on Oct. 26, 2000, now Pat. No. 6,479,677.

(51) Int. Cl.[7] ................. C07D 307/44; C07D 307/12
(52) U.S. Cl. ................. 549/503; 549/429; 549/497; 549/505; 549/506
(58) Field of Search ................. 549/503, 429, 549/497, 505, 506

(56) References Cited

U.S. PATENT DOCUMENTS

| | | | |
|---|---|---|---|
| 1,739,919 A | 12/1929 | Ricard et al. | |
| 2,273,484 A | 2/1942 | Guinot | |
| 2,456,187 A | 12/1948 | Guinot | |
| 3,021,342 A | 2/1962 | Manly | |
| 5,912,364 A | 6/1999 | Beavers | |
| 6,479,677 B1 * | 11/2002 | Ahmed | 549/506 |

OTHER PUBLICATIONS

Burnette et al., "Production of 2–Methylfuran by Vapor–Phase Hydrogenation of Furfural," I&EC, 40 (3):502–505 (1948).

Brown et al., "Vapor Phase Hydrogenation of Furfural to Furfuryl Alcohol," I&EC, 40 (3):1382–1385 (1949).

* cited by examiner

Primary Examiner—Ba K. Trinh
(74) Attorney, Agent, or Firm—Todd E. Garabedian; Wiggin and Dana LLP

(57) ABSTRACT

Processes are disclosed for the preparation of 2-methylfuran and 2-methyltetrahydrofuran. The continuous vapor-phase processes are commercially viable and efficient because they permit the preparation of 2-methylfuran and 2-methyltetrahydrofuran using commercially-available catalysts, namely, a reduced copper-based catalyst consisting essentially of cupric oxide, chromium (III) oxide, manganese oxide and barium chromate and a reduced nickel-based catalyst consisting essentially of nickel, nickel (II) oxide, aluminum oxide and silica. An apparatus comprising two inline hydrogenators is used for preparing the 2-methylfuran or 2-methyltetrahydrofuran.

5 Claims, 2 Drawing Sheets

PROCESSES FOR THE PREPARATION OF 2-METHYLFURAN AND 2-METHYLTETRAHYDROFURAN

CROSS-REFERENCE

This application is a continuation of Ser. No. 09/697,240, filed Oct. 26, 2000, now U.S. Pat. No. 6,479,677.

FIELD OF INVENTION

This invention relates to processes for the preparation of 2-methylfuran and 2-methyltetrahydrofuran.

BACKGROUND OF THE INVENTION

The catalytic hydrogenation of furfural can lead to numerous derivatives, including furfuryl alcohol ("FA"), 2-methylfuran ("2-MF") and 2-methyltetrahydrofuran ("2-MTHF"). Those skilled in the art recognize that there is a substantial commercial market for processes that efficiently produce furfural derivatives, such as FA, 2-MF and 2-MTHF, because they are marketable as specialty chemical products. For example, 2-MTHF is useful as a component of certain alternative fuel compositions that are cleaner burning than present liquid fuels. Currently, there are only a few commercial-scale production facilities for 2-MF and 2-MTHF because there is a lack of economically-viable methods for their preparation.

Some of the reaction pathways for the catalytic hydrogenation of furfural to various furfural derivatives are illustrated below.

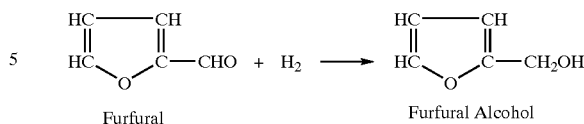

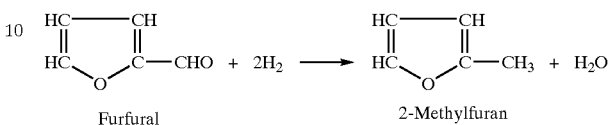

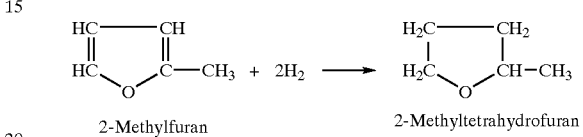

Although both liquid-phase and vapor-phase hydrogenation of furfural are possible, the majority of the previous studies were focused on developing processes for the liquid-phase hydrogenation of furfural. Although liquid-phase hydrogenation to produce 2-MTHF is theoretically possible, no literature was found which reported a successful use of a liquid-phase hydrogenation process to produce 2-MTHF. Sometimes 2-MF was created, but often as a by-product, FA being one of the primary products of the liquid-phase

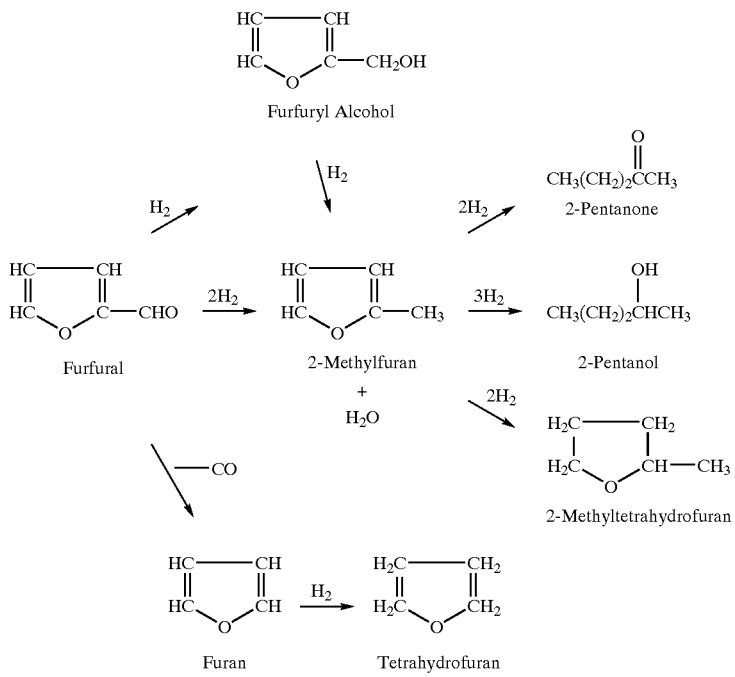

Since the early part of the twentieth century, researchers have investigated the mechanisms of individual reaction pathways that start with the catalytic hydrogenation of furfural.

Several of the previously studied reaction pathways are illustrated below, namely, pathways for the production of FA, 2-MF and 2-MTHF.

hydrogenation. The liquid-phase hydrogenations were most often run batch-wise in the laboratory and produced relatively small amounts of product, in part due to inherent defects associated with the custom-made catalysts, such as prohibitive preparation costs and inconsistent preparations, that led to inconsistent yield or purity of the products formed.

In addition, the liquid-phase hydrogenations were often run at greater-than-atmospheric pressure and used specialized equipment capable of operating at elevated pressures. As a result of these and other limitations, liquid-phase hydrogenations were not easily scaled up beyond the laboratory bench level, were difficult to control and required large amounts of energy to complete, thus reducing the overall efficiency and yield of liquid-phase hydrogenation processes. The chart below summarizes some general differences between liquid-phase hydrogenations and vapor-phase hydrogenations.

|  | Liquid-phase Hydrogenation | Vapor-phase Hydrogenation |
|---|---|---|
| Pressure | high | low or atmospheric |
| Scaleable | difficult | easier |
| Process | batch-type | batch-type or continuous |
| Process control | difficult | easier |
| Catalyst recovery | required | not required |
| Reactor | high-pressure vessel | packed-column, tray tower |
| F to 2-MF Yields | low | quantitative |
| 2-MF to 2-MTHF Yields | not known in many instances | moderate to high |
| Products | complex mixture | fewer, easily separated by products |

The following references reported the results of research conducted in the area of vapor-phase, catalytic hydrogenation of furfural.

U.S. Pat. No. 1,739,919, issued Dec. 17, 1929 to Ricard and Guinot, disclosed a process for "the manufacture of furfuryl alcohol and methylfurane [sic]." The furfural feedstock was vaporized and mixed in a vaporizer with a current of hot hydrogen gas. The furfural vapor and hydrogen gas mixture was delivered into a "catalyzing furnace" packed with a reduced copper oxide catalyst. The custom-made catalyst was prepared in the laboratory by "precipitation and calcination" and a "backing substance" such as asbestos, pumice stone, silica or kaolin, was used to provide support for the catalyst during the reaction. The vapor-phase hydrogenation was run with fresh catalyst at atmospheric pressure and at a temperature of 140° C. The vapor issuing from the "catalyzing furnace" was passed through a condenser. The condensed liquids were a mixture of methylfuran, furfural, furfuryl alcohol and water. The methylfuran was removed from the mixture by simple distillation. The proportion of methylfuran was 10 to 20 percent of the furfuryl alcohol formed."

U.S. Pat. No. 2,273,484, issued Feb. 17, 1942 to Guinot, disclosed a process "for manufacturing synthetic rubber from furfurol [sic]." One aspect of the invention was using a vapor-phase hydrogenation to convert furfural to methylfuran using a copper catalyst. The methylfuran obtained from this hydrogenation was then passed as vapor over a reduced nickel catalyst at a temperature of 120° C. to produce a mixture of products, including 85 percent MTHF. No other details regarding the conditions of the processes were disclosed.

U.S. Pat. No. 2,456,187, issued Dec. 14, 1948 to Guinot, disclosed a process for catalytically hydrogenating organic substances. In one example, furfural was hydrogenated using "pure copper obtained by reducing oxide thereof." The custom-made catalyst was made in the laboratory of copper oxide precipitated on an inert carrier such as asbestos, silica or pumice. The catalyst and method of using the same were designed in an attempt to prevent problems with undesired local elevations of temperature during the reduction of the catalyst or during the hydrogenation. Vaporized furfural was mixed with hydrogen and delivered into an apparatus containing bundles of tubes packed with tablets of the catalyst. The hydrogenation was performed at a temperature of 170° C. and the product mixture was condensed, consisting mostly of furfuryl alcohol (60 percent) as well as some methylfuran (40 percent). In addition, methylfuran was produced by hydrogenation of furfuryl alcohol at a temperature of 170° C.

In 1948, Burnette et al. studied twenty-three custom-made catalysts prepared in the laboratory for use in the production of 2-MF by vapor-phase hydrogenation of furfural. See Burnette et al., "Production of 2-Methylfuran by Vapor-Phase Hydrogenation of Furfural," I&EC, 40 (3):502–505 (1948). The paper noted that "the primary object of almost all previous work on the hydrogenation of furfural has been the production of furfuryl or tetrahydrofurfuryl alcohol." Id. at 502. The best laboratory-scale (15 to 100 grams of furfural) yields of 2-MF (99.5 percent) resulted when a copper chromite catalyst (dispersed on activated charcoal) was used and a temperature of 225° C. was maintained during the hydrogenation. However, the yields (grams of 2-MF produced/grams of furfural hydrogenated) of 2-MF produced as a result of a larger (500 grams of furfural) work-up of this process were much lower, varying from 67–80 percent. Problems noted by the researchers during the scale-up of the process included the almost total deactivation of the catalyst after 7 days of nominal usage and a 20° C. to 30° C. temperature variation between the center of the catalyst bed and the reactor wall. These problems caused the overall efficiency and economic viability of the reaction to be reduced.

Later, this same laboratory reported using the same type catalyst to produce high yields of furfuryl alcohol. After careful consideration of various factors impacting the reaction, the researchers concluded that the temperature variable was the most critical. In these later experiments, furfural was vaporized and mixed with hydrogen (in a molar ratio of hydrogen to furfural in excess of 20:1) and then delivered into a reactor tube heated to between 130° C. to 135° C. and containing a copper chromite catalyst supported on charcoal. They catalyst bed temperature was reported in some experiments to be as low as 112° C. and in other experiments as high as 192° C. In all experiments, the primary product was furfuryl alcohol (recovered in yields widely ranging from 26 to 93 percent) and 2-MF was collected as a by-product. See Brown et al., "Vapor Phase Hydrogenation of Furfural to Furfuryl Alcohol," I&EC, 40 (3):1382–1385 (1949).

U.S. Pat. No. 3,021,342, issued Feb. 13, 1962 to Manly disclosed hydrogenation of pyrans and furans, including the vapor-phase hydrogenation of methylfuran to produce methyltetrahydrofuran, preferably using a custom-made, reduced nickel hydrate catalyst. The methylfuran, containing pyridine as a selective poison for the catalyst, was vaporized and blended into a stream of preheated hydrogen gas. The resulting methylfuran/hydrogen vapor mixture was passed through a catalyst column and the reaction products were collected and condensed. The hydrogenation was run at a preferred temperature range of 60° C. to 65° C. The reaction occurred at about or in slight excess of atmospheric pressure. Conversion of the methylfuran was almost 100 percent and the product analyzed about 98.4 percent, by weight methyltetrahydrofuran.

These results reported by researchers in the area of vapor-phase, catalytic hydrogenation of furfural demonstrate that significant effort was required to find appropriate catalysts and reaction conditions that direct the vapor-phase, catalytic hydrogenation of furfural along a particular reaction pathway towards the production of a desired furfural hydrogenation derivative. Those skilled in the art recognize that an even greater amount of experimentation would be required to find particular combinations of catalysts and reaction conditions necessary to produce furfural hydrogenation derivatives in both high yields and with high purity in an economic and commercially-viable manner.

Prior attempts to develop processes for the vapor-phase, catalytic hydrogenation of furfural, including those described above, had one or more of the following disadvantages: low yields and/or low purity of 2-MF and/or 2-MTHF, low conversion of furfural to 2-MF and 2-MTHF and/or of 2-MF to 2-MTHF, production of undesirable by-products, production of by-products that were difficult to separate from the desired products, high process costs due to the low efficiency of the catalysts and/or due to the short life of the catalysts and an inability to sufficiently control the temperature during the hydrogenations.

In addition, because the catalysts used in these prior art attempts were prepared in small quantities in the individual laboratories, the results obtained using such catalysts were inconsistent and the possibility of commercial-scale processes was precluded. The custom, small-scale preparation of such catalysts often led to inconsistent catalyst quality and lowered yields and purity of the desired products. Thus, there is a continuing need for commercially-viable, high-yield furfural vapor-phase hydrogenation processes which efficiently produce pure products, including furfural derivatives, such as 2-MF and 2-MTHF, using commercially available, low-cost catalysts.

SUMMARY OF THE INVENTION

The present invention provides processes for the preparation of 2-methylfuran ("2-MF") and 2-methyltetrahydrofuran ("2-MTHF"). The processes of the invention are commercially viable because they permit the preparation of 2-MF and 2-MTHF using high-yield furfural vapor-phase hydrogenation processes which efficiently produce pure products using commercially-available catalysts. It has been found that careful selection of the catalyst used in the vapor-phase hydrogenation as well as careful monitoring and control of selected reaction parameters, including vaporization temperature, reaction temperature and molar ratios of the reactants, can result in successfully directing the vapor-phase, catalytic hydrogenation of furfural of high yields of pure 2-MF and 2-MTHF. The 2-MTHF so produced has desired properties that make it useful as a co-solvent in a spark ignition motor fuel composition that is an alternative to currently available gasoline motor fuels based on refined crude oil. For example, see the disclosure in U.S. Pat. No. 5,697,989, issued Dec. 16, 1997 to Paul, which is incorporated herein by referenced.

In one embodiment, a vapor-phase, catalytic hydrogenation process for the conversion of furfural to 2-MTHF is provided. The process comprises the steps of (a) vaporizing a furfural-containing feedstock; (b) mixing and hydrogenating the vaporized feedstock with sufficient hydrogen to provide about 2 moles of hydrogen per mole of furfural in the feedstock, the mixing and hydrogenating being carried out at a temperature at or above 175° C. in the presence of a reduced copper-based catalyst consisting essentially of cupric oxide, chromium (III) oxide, manganese oxide, and barium chromate to produce a first vaporous mixture of hydrogenated products including 2-MF; (c) mixing the first vaporous mixture with sufficient hydrogen to provide about 2 moles of hydrogen per mole of 2-MF in the first vaporous mixture, the mixing and hydrogenating being carried out at a temperature at or above about 100° C. in the presence of a reduced nickel-based catalyst consisting essentially of nickel, nickel (II) oxide, aluminum oxide, and silica to produce a second vaporous mixture of hydrogenated products including 2-MTHF; (d) condensing the second vaporous mixture; (e) allowing the condensate to separate into an aqueous phase and an organic phase; and (f) separating the organic phase to recover the 2-MTHF.

Another embodiment of the above process for the vapor-phase, catalytic hydrogenation of furfural to 2-MTHF includes the steps described above and the optional steps of condensing all or a portion of the first vaporous mixture of hydrogenated products including 2-MF to produce a condensate, allowing the condensate to separate into an aqueous phase and an organic phase, and then recovering 2-MF, which can be used as a 2-MF feedstock for mixing with sufficient hydrogen to provide about 2 moles of hydrogen per mole of 2-MF, as described in step (c) of the embodiment of the preceding paragraph, to produce a second vaporous mixture of hydrogenated products including 2-MTHF.

Yet another embodiment of the above process for the vapor-phase, catalytic hydrogenation of furfural to 2-MTHF includes the steps described above and the optional steps of recycling the second vaporous mixture of hydrogenated products including 2-MTHF by mixing all or a portion of the second vaporous mixture of hydrogenated products including 2-MTHF with sufficient hydrogen to provide about 2 moles of hydrogen per mole of unreacted 2-MF remaining in the second vaporous mixture, the mixing and hydrogenating being carried out at a temperature at or above about 100° C. in the presence of a reduced nickel-based catalyst consisting essentially of nickel, nickel (II) oxide, aluminum oxide, and silica to produce a third vaporous mixture of hydrogenated products including 2-MTHF, condensing the third vaporous mixture, allowing the condensate to separate into an aqueous phase and an organic phase and separating the organic phase to recover the 2-MTHF.

A second embodiment of the invention provides a process for the vapor-phase, catalytic hydrogenation of furfural to 2-MF. The process comprises the steps of: (a) vaporizing a furfural-containing feedstock; (b) mixing and hydrogenating the vaporized feedstock with sufficient hydrogen to provide about 2 moles of hydrogen per mole of furfural in the feedstock; the mixing and hydrogenating being carried out at a temperature at or above 175° C. in the presence of a reduced copper-based catalyst consisting essentially of cupric oxide, chromium (III) oxide, manganese oxide, and barium chromate to produce a vaporous mixture of hydrogenated products including 2-MF; (c) condensing the vaporous mixture; (d) allowing the condensate to separate into an aqueous phase and an organic phase; and (e) separating the organic phase to recover the 2-MF.

The present invention has several advantages, including, but not limited to the following:

2-MF and 2-MTHF are efficiently produced using commercially-available catalysts, which are generally lower in cost and of a more consistent composition than custom-made catalysts;

2-MF and 2-MTHF are efficiently produced using vapor-phase, catalytic hydrogenation processes wherein the furfural feedstock does not need to be purified prior to the vapor-phase hydrogenation, thus allowing for the use of furfural from non-commercial sources, such as furfural derived from biomass;

the vapor-phase, catalytic hydrogenation of furfural is carried out at low to moderate temperatures and low to about atmospheric pressures, thereby eliminating the expensive equipment and increased energy requirements needed for high-temperature, high-pressure processes;

the use of fixed-bed, sieve-tray, vapor-phase, catalytic hydrogenators rather than catalyst-packed columns allows for easier scale-up from laboratory to pilot plant to commercial facility and also allows for more precise control of the reaction conditions, such as reactor temperatures;

the processes are flexible in that the type and amount of vapor-phase hydrogenation end-products can be altered by changing process conditions, for example, temperature, without changing the catalyst(s);

high yields of substantially pure products, such as, 2-MF and 2-MTHF, and high conversion rates from starting materials to end-products are achieved; and by-products can be easily and efficiently separated from the desired products by stepwise cooling based upon differences in boiling points.

BRIEF DESCRIPTION OF THE DRAWINGS

For the purpose of illustrating the invention, the drawings show a form of the invention that is presently preferred. However, it should be understood that the present invention is not limited to the precise arrangements and instrumentalities shown in the drawings, wherein.

DETAILED DESCRIPTION OF THE INVENTION

Figure 1:
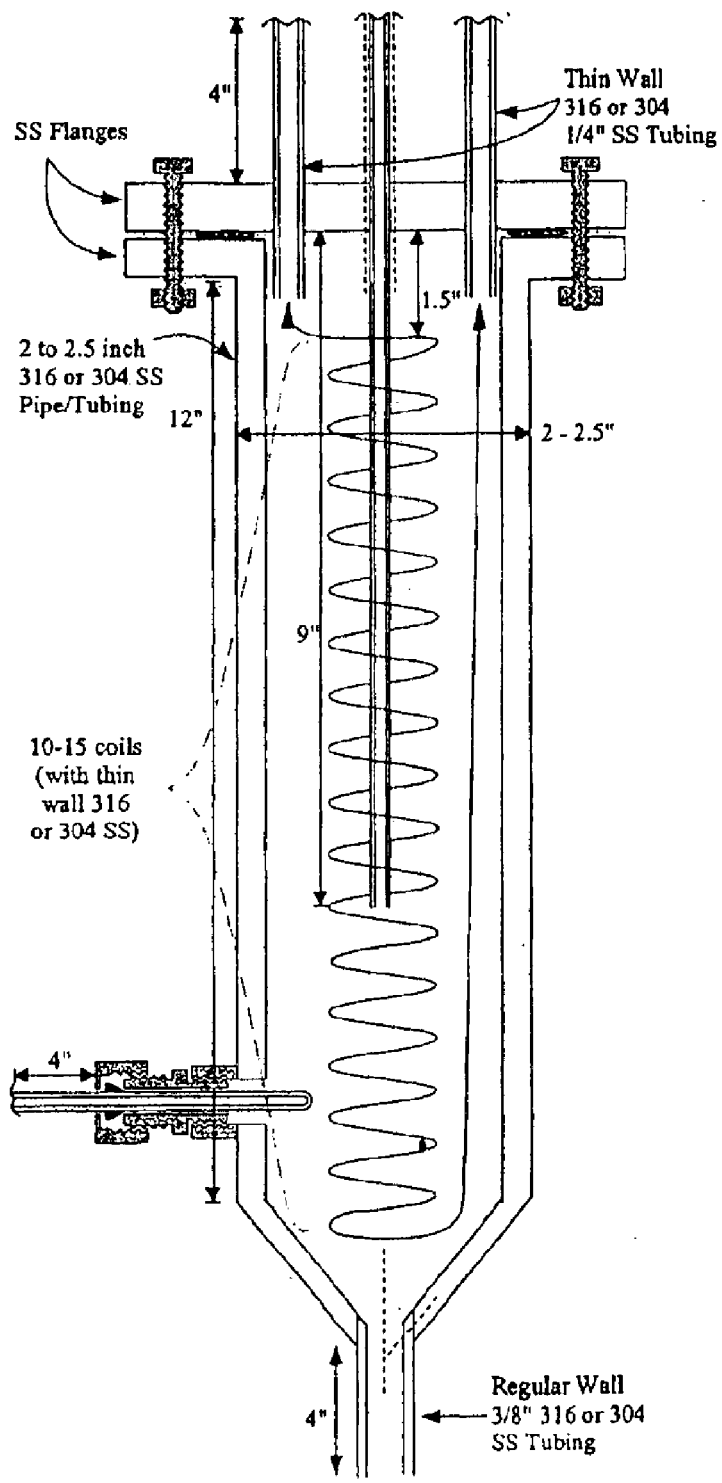
FIG. 1 is a schematic diagram illustrating the design of the vaporizer used for the vapor-phase, catalytic hydrogenation of furfural in the present invention.

The commercially-viable, high-yield, furfural vapor-phase hydrogenation processes of the present invention provide for the efficient preparation and easy recovery of pure 2-methylfuran ("2-MF") and 2-methyltetrahydrofuran ("2-MTHF") using commercially-available catalysts. As used herein, the term "reactor" is meant to include a reactor specifically used for hydrogenation, and in particular vapor-phase hydrogenation, and is equivalent to the term "hydrogenator" used interchangeably herein. The terms "hydrogenation" and/or "hydrogenating" are used in their ordinary sense and are meant to include a reaction of hydrogen with an organic compound and includes vapor-phase, catalytic hydrogenation reactions.

In the preferred process, the catalytic, vapor-phase hydrogenation of furfural is performed continuously at about atmospheric pressure using a two-stage system having two reactors connected in series, wherein a vaporized furfural-containing feedstock is mixed and hydrogenated in a first reactor to produce a first vaporous mixture of hydrogenated products, including 2-MF, and then the first vaporous mixture is mixed and hydrogenated in a second reactor to produce a second vaporous mixture of hydrogenated products, including 2-MTHF. Performing the vapor-phase, catalytic hydrogenations in a continuous manner provides an efficient use of equipment and materials. Both the first and the second vapor-phase, catalytic hydrogenations are carried out at about atmospheric pressure, which is advantageous because of the elimination of the high costs associated with the use of high-pressure equipment. In addition, both the first and the second vapor-phase, catalytic hydrogenations are carried out in a closed system so that losses due to evaporation are reduced.

The vaporous mixtures of hydrogenated products exiting from the first or second reactors may be separated by methods well-known to those skilled in the art, such as, condensation, molecular sieves or by simple distillation based upon differences in boiling points between the desired products and any undesired byproducts or unreacted starting material. Preferably, the 2-MTHF is recovered by allowing the second vaporous mixture to separate into two phases, namely, an organic phase and an aqueous phase, and collecting 2-MTHF from the organic phase. Preferably, the 2-MF is similarly recovered by allowing all or a portion of the first vaporous mixture to separate into two phases, that is, an organic phase containing 2-MF and an aqueous phase containing FA. The 2-MF recovered is free of FA and can be used as a purified 2-MF feedstock for the second vapor-phase, catalytic hydrogenation or retained as a separate valuable product. The FA remaining in the aqueous phase also can be collected as a separate valuable product. Preferably, a buffer system is used when diverting a portion of the first vaporous mixture so that the quantity of remaining first vaporous mixture that is directed into the second hydrogenator is controlled and mixed with sufficient hydrogen to provide about two moles of hydrogen per mole of 2-MF in the first vaporous mixture.

According to the methods well-known to those skilled in the art, the throughput of the processes of the invention can easily be increased without undue experimentation, for example, by using a larger equipment set-up or by using multiple smaller equipment set-ups connected in serial or in parallel.

Preferably, the first reactor contains a supported perforated plate upon which is placed the reduced copper-based catalyst, as described in detail below, useful for the vapor-phase, catalytic hydrogenation of furfural to 2-MF. Preferably, the second reactor contains a supported perforated plate upon which is placed the reduced nickel-based catalyst, as described in detail below, useful in the vapor-phase, catalytic hydrogenation of 2-MF to 2-MTHF.

It has been found that there are several factors that are important to the processes of the present invention, for example, the careful selection of the copper-based and nickel-based catalysts and the careful monitoring and control of the temperatures of the reactants of the two vapor-phase hydrogenations within an optimal range. Since the vapor-phase, catalytic hydrogenation of furfural is an exothermic reaction, insufficient control of the process temperatures produces areas of excessively elevated temperatures, resulting in less efficient or deactivated catalysts. The reaction efficiency is greatly increased by maintaining the activity of the catalysts at their most active and selective state. If the temperature within either reactor is allowed to fall below the dew point of any of the reactants or products, then the vapors of these reactants or products will condense and the resulting liquid will reduce the efficiency of the processes.

The present invention overcomes this heat transfer challenge because the hydrogenators and vaporizers are wrapped with insulated jackets and because they are connected so that there is minimal distance between them, decreasing the heat loss of the vapors being delivered from the vaporizers into the hydrogenators.

It is especially preferred that the reaction beds of the hydrogenators and vaporizers be maintained at optimal, consistent temperatures, as described in detail below. Preferably, the temperature within the hydrogenators and vaporizers is closely monitored by a plurality of thermocouples inserted into a plurality of thermowells located along the length of the hydrogenators and vaporizers. The thermocouples are connected to a suitable measuring instrument for use as thermometers. Preferably, the temperature data from the thermocouples is interfaced with a computer-controlled regulator that allows for heat to either be applied or removed from the hydrogenators and vaporizers, resulting in real time temperature regulation. In this way, the precise temperature within the hydrogenators can be determined and modified as needed to maintain the highest efficiency of the reaction by preventing any damage to the catalyst that could be caused by overheating and by preventing the vapors within the reactors from condensing. As a result, the overall efficiency of the processes of the invention is increased by reducing the formation of a heat gradient within the hydrogenators and the vaporizers.

Preferably, because the processes within the reactors are exothermic, any heat determined to be in excess of that required for high efficiency of the processes can be directed away from the reactors for use elsewhere by using cooling coils wrapped in and/or around the reactors or other appropriate means. In this way, the overall efficiency of the processes is enhanced by reducing the need for an externally-derived source for heat energy.

Better control of process parameters, including temperatures within the reactors and the vaporizes and flow rates and molar ratios of the reactants provide improved yields and conversion rates for the desired vapor-phase, catalytic hydrogenation products, namely, 2-MF and 2-MTHF, which has a positive impact on the efficiency and economics of the processes of the present invention. Careful control of such process parameters provides for increased flexibility of the processes by allowing, for example, subtle modifications to the flow rates and molar ratios of the reactants, which results in changes of the composition of the end products. In another example, the amount of FA obtained from the first vapor-phase hydrogenation can be increased without changing the copper-based catalyst and by using the same furfural feedstock, but by adjusting the temperature, for example, to about 135° C. or to about 155° C. This temperature change results in very high conversions of furfural to FA. In yet another example, the amount of THFA obtained from the second vapor-phase hydrogenation can be increased without changing the nickel-based catalyst and by using the same 2-MF feedstock, but by adjusting the temperature, for example, to about 125° C. to about 155° C. This temperature change results in an increased amount of THFA obtained from the second vapor-phase hydrogenation. As a result, a production facility where the processes of the invention are run can have increased flexibility because carefully controlled modifications to selected process parameters can result in the production of alternative end products.

The various process parameters are interrelated in that modifications of one impacts another. For example, the temperature of the processes is related to the flow rates of the reactants of the vapor-phase hydrogenations. An increase in the flow rates of the reactants into the vaporizer will require an increase in temperature within the vaporizer to ensure that the additional moles of reactants being added are fully vaporized. The present invention provides that the molar ratios of the reactants are properly balanced so that there is optimal combining and complete vaporization leading to the desired products in the highest yields and conversion rates. Preferably, the molar ratio of hydrogen to furfural in the first vapor-phase, catalytic hydrogenation and of the hydrogen to 2-MF in the second vapor-phase, catalytic hydrogenation is about 2:1.

The desired products of the first and second vapor-phase, catalytic hydrogenations, 2-MF and 2-MTHF respectively, may be collected by first condensing the vaporous product streams exiting the respective reactors to below the dew point of the products. Specifically, the vapor stream from the first hydrogenation may be cooled resulting in a liquid having an organic phase containing 2-MF as the major product and an aqueous phase containing FA as a major component. As a result, because of this simple separation, there is a reduction in the cost of recovery and/or purification of 2-MF. 2-MTHF may preferably be recovered from the vapor stream from the second hydrogenation by simple distillation. Preferably, one or more glass condensers, for example Friedrichs glass condensers, cooled to about −10° C. are used for condensation of the vapor streams. Preferably, any excess vapors exiting the condensers can be directed through a series of traps prior to venting to the atmosphere. Most preferably, these traps utilize a sequence of a dry ice/ethanol bath, a methanol bath and/or an ice bath. The use of these traps allows the processes of the invention to be performed in a closed atmosphere, which reduces potential loses of volatile compounds due to evaporation.

In the preferred process, the furfural-containing feedstock is delivered through a feed line surrounded by heating coils to improve vaporization efficiency and the heating coils are maintained at or above about 175° C. The feed line extends into the center of a first vaporizer having the form of a vertical cylinder with a tapered end. The tapered end of the first vaporizer is preferably directly attached by compression fittings to the first reactor. The first vaporizer may be steam-heated, electric-heated, or may be heated by heat recovered from other parts of the production facility where the processes of the invention are being run. The temperature within the first vaporizer is closely monitored via one or more thermocouples inserted into thermowells extending through the wall of the first vaporizer chamber and into the center of the first vaporizer chamber near the end of the feed line. The furfural-containing feedstock is combined in the first vaporizer with hydrogen gas delivered into the first vaporizer through a separate line, thus producing a first vaporous mixture. The flow rates of both the furfural-containing feedstock and the hydrogen are closely monitored and controlled within selected optimal ranges so that there is about 2 moles of hydrogen per mole of furfural in the feedstock. The tapered end of the first vaporizer reduces holdup and improves the delivery of the first vaporous mixture into the first reactor.

In the preferred process, the first vaporous mixture is delivered into a first tubular, vertical hydrogenator that is maintained at or above about 175° C. and having a feed end and a tapered outlet end. It is especially preferred that the temperature be maintained at about 195° C. to about 200° C. The feed end of the first reactor is directly attached by compression fittings to the tapered end of the first vaporizer. The first reactor contains a perforated plate that holds a reduced copper-based catalyst consisting essentially of cupric oxide, chromium (III) oxide, manganese oxide, and barium chromate. Preferably, the first reactor is vertically oriented inline with the first vaporizer, such that the tapered end of the first vaporizer delivers the first vaporous mixture into the feed end of the first reactor.

In the preferred process, the first vaporous mixture including 2-MF is delivered from the tapered outlet end of the first hydrogenator into the center of a second vaporizer that is similar in form to the first vaporizer. For example, the second vaporizer has heating coils around the tube delivering the first vaporous mixture. The first vaporous mixture including 2-MF is delivered into a second tubular, vertical hydrogenator, preferably of a form similar to that of the first hydrogenator. In a manner similar to the set-up described above for the first hydrogenator, the temperature within the second hydrogenator is preferably controlled and monitored, using a plurality of thermowells, insulation, and cooling coils, so that the temperature is carefully maintained at or above about 100° C. It is especially preferred that the temperature be maintained at about 115° C. to about 130° C. The second hydrogenator has a feed end directly attached by compression fittings to the tapered end of the second vaporizer and has a tapered outlet end with a flanged product outlet, from which is delivered the second vaporous mixture. The second hydrogenator contains a reduced nickel-based catalyst consisting essentially of nickel, nickel (II) oxide, aluminum oxide and silica on a perforated plate supported therein. The catalytic hydrogenation of the first vaporous mixture produces a second vaporous mixture including 2-MTHF. The second vaporous mixture including 2-MTHF may then condensed to produce a condensate, preferably by being passed through at least one Friedrichs glass condenser maintained at a temperature of about −10° C. This condensate may be allowed to separate into two phases, namely, an organic and an aqueous phase, from which 2-MTHF is recovered from the organic phase. Preferably, 2-MF is recovered in a manner similar to that described above for 2-MTHF, in that the first vaporous mixture including 2-MF is condensed to produce a condensate, for example, by being passed through at least one Friedrichs glass condenser maintained at a temperature of about −10° C. This condensate is allowed to separate into two phases, namely, an organic and an aqueous phase, from which 2-MF is recovered from the organic phase. The 2-MF so collected is FA-free and can be vaporized and delivered into the second hydrogenator to produce high yields of 2-MTHF with very low concentrations of 2-pentanone, 2-pentanol, and tetrahydrofurfuryl alcohol. Alternatively, the 2-MF so collected can be sold as a specialty chemical. Preferably, the first vaporous mixture including 2-MF is continuously delivered directly from the first hydrogenation to the second hydrogenation.

If the furfural-containing feedstock is purchased commercially, it may be in a rather purified state. Commercial sources of furfural include Sigma-Aldrich Chemical Co. (Milwaukee, Wis.), QO Chemical, Inc. (Omaha, Nebr.), and Great Lakes Chemical Corp. (Memphis, Tenn.). In the processes of the invention, the furfural-containing feedstock may be used without purification. For example, the furfural-containing feedstock may be derived from biomass using, for example, a hydrolysis process. Preferably, the water content of the furfural-containing feedstock is below about 5 percent, most preferably below about 1 percent. In addition, the processes of the invention are flexible enough to allow for their incorporation into an integrated process system, that is, the processes of the invention using a biomass-derived furfural-containing feedstock can be combined with other processes into a single, integrated biorefinery system that encompasses the conversion of the biomass into final products, such as 2-MF and 2-MTHF. For example, the types and quantities of furfural derivatives produced by the integrated system could closely match the types and quantities needed for a particular application, including using the furfural derivatives obtained by the processes of the invention as components of a fuel blend. Such an integrated process system would include processes for the production of the furfural-containing feedstock from biomass, then using that furfural-containing feedstock in the processes of the invention for the preparation of furfural derivatives, such as 2-MF and 2-MTHF. An integrated process system using the efficient processes of the invention would have improved economics because of the more efficient use of materials and minimization of waste.

The theoretical furfural content of selected biomass raw materials is shown in the table below. See Dunlop, A. P. & Peters, F. N. (1953), in Chapter 8: Furfural—Production, Analytical Methods and Physical Properties, *American Chemical Society Monograph Series Edition*. (Dunlop, A. P. & Peters, F. N., Eds.). pp. 272–331, Reinhold Publishing Corporation, New York.

| Raw Material | Average Furfural Content, % dry basis |
|---|---|
| Corn Cobs | 23.4 |
| Oat Hulls (cleaned) | 22.3 |
| Cottonseed Hull Bran | 21.2 |
| Cottonseed Hulls | 18.6 |
| Bagasse | 17.4 |
| Rice Hulls | 11.4 |

Biomass raw materials, including cellulose, hemicellulose, lignin, lignocellulose and starch may be converted into sugars using, for example, hydrolysis, such that any hemicellulose is converted into primarily xylose and the cellulose is converted primarily into glucose. Further bioprocessing of the glucose and/or the xylose can produce ethanol that can be useful as a component of a blended fuel. The xylose can also be further thermochemically processed into furfuryl and water, as illustrated by the reaction pathway shown below.

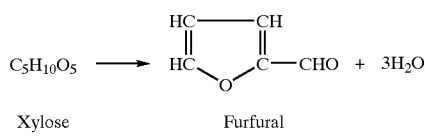

C$_5$H$_{10}$O$_5$ (Xylose) → Furfural + 3H$_2$O

The resulting furfural mixture can then concentrated by means known to skilled workers, for example, by distillation. This concentrated furfural-containing feedstock can then be used directly in the processes of the present invention to produce 2-MF and 2-MTHF. Any lignin residue separated from the sugars following hydrolysis can undergo separate thermochemical processing to produce fractionation chemicals or can be used to generate electricity. The diagram below presents a flowchart summarizing these pathways.

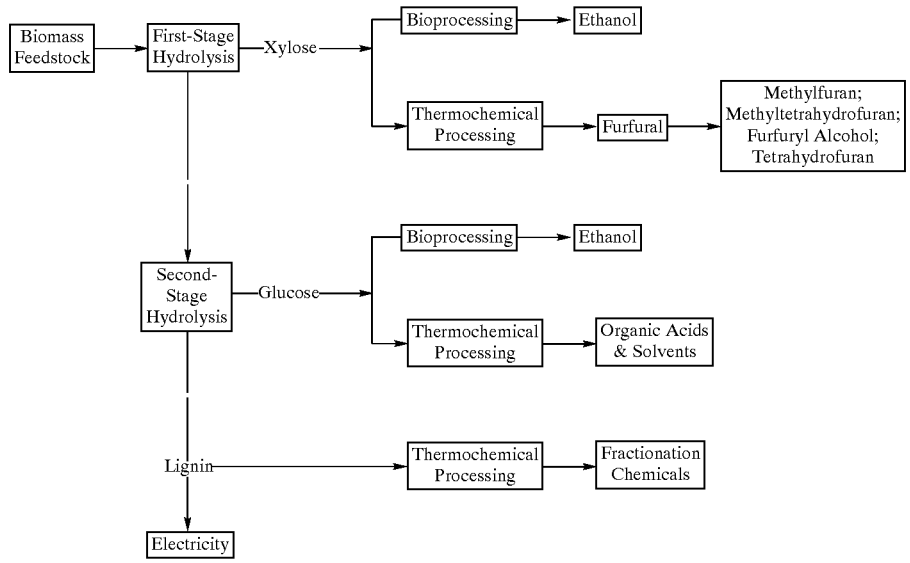

It has been found that when the second vapor-phase hydrogenation is run at lower temperatures, such as less than about 115° C., the amount of unreacted 2-MF present in the second vaporous mixture increases. In such a case, recycling the second vaporous mixture including unreacted 2-ME through the second reactor can increase the percentage of 2-MTHF in the final product. It also has been found that if the second vapor-phase hydrogenation is run at higher temperatures, such as higher than about 130° C., there is complete conversion of the 2-MB to 2-MTHF and recycling of the second vaporous mixture is not necessary.

Exemplary catalysts, both further described herein, include a copper-based catalyst for use in the first vapor-phase hydrogenation and a nickel-based catalyst for use in the second vapor-phase hydrogenation. The catalysts used for the first and second vapor-phase hydrogenations are finely divided metals or metallic compounds which have a large surface area. Preferably, they are activated prior to their use according to the manufacturers specifications. Suitable carriers include active carbon, aluminum oxides, titanium oxides, magnesium or aluminum silicates, and zirconium dioxide. The availability of a commercial source for the catalysts of the processes of the invention results in an economic advantage as well as increasing the consistency of the vapor-phase hydrogenations. The catalysts that may be used with the invention are less expensive, in part, because they do not contain any precious metals, such as, platinum or palladium. Particular advantages of the copper-based catalyst include no sensitivity to sulfur-or halogen-containing impurities, a reduced sensitivity toward deactivation, no special apparatus (e.g. reduction furnace) needed, fresh preparation not required, stabile even in contact with air or moisture, small quantity required for reaction, reduced labor-intensive preparation and can be used repeatedly.

It has been found that the form and size of the catalyst used has an effect on the surface area of the catalyst that is available for vapor-phase hydrogenation of furfural into 2-MF and 2-MTHF. Typically, catalysts are available in a variety of forms and sizes, for example, as powders or tablets. It has been found that the form and size of the catalyst selected for the vapor-phase hydrogenation of furfural has an impact on the reaction bed porosity that causes an effect on the temperature within the reactors and on control of the reaction temperatures within the first and second vapor-phase hydrogenations. While a catalyst in powder form results in the largest surface area, such a form interferes with the flow of vapors during the hydrogenations and make careful control of the reaction temperature in the first and second hydrogenators impractical. It is preferred that the copper-based catalyst used for the first vapor-phase hydrogenation be in the form of tablets that have dimensions between about 3 millimeters by 3 millimeters ("mm") to about 6 by 6 mm, for example, 3 by 3 mm, 4.5 by 3 mm, 4.5 by 4.5 mm, or 6 by 6 mm. The most preferred copper-based catalyst is in tablet form with dimensions of 3 by 3 mm. It is also preferred that the nickel-based catalyst used for the second vapor-phase hydrogenation be in the form of tablets that have dimensions between about 3 by 3 mm to about 6 by 6 mm, for example, 3 by 3 mm, 4.5 by 4.5 mm, or 6 by 3 mm. The most preferred nickel-based catalyst is in tablet form with dimensions of 3 by 3 mm.

In one embodiment, the reduced copper-based catalyst for the first vapor-phase hydrogenation consists essentially of a mixture of cupric oxide, chromium (III) oxide, manganese oxide, and barium chromate. The composition of the preferred copper-based catalyst is about 47 percent cupric oxide, about 46 percent chromium (III) oxide, about 4 percent manganese oxide, about 3 percent barium chromate and small amounts (0.2 percent) of moisture that may be bonded water in the actual metal oxide or catalyst matrix, with weights totaling 100 percent. The barium and manganese elements act as promoters. A particularly useful copper-based catalyst for the first vapor-phase hydrogenation is product number G-99B-0 which can be obtained from United Catalysts, Inc. (Louisville, Ky.). Before use in the first vapor-phase hydrogenation, the copper-based catalyst is reduced over a period of about five hours according to the manufacturer's instructions, within the first hydrogenator at a temperature of about 150° C. to about 200° C. using a mixture of nitrogen and hydrogen. Reduction of the copper-based catalyst is preferably carried out in situ prior to the beginning of the first vapor-phase hydrogenation.

In the preferred embodiment, the reduced nickel-based catalyst for the second vapor-phase hydrogenation consists essentially of nickel, nickel (II) oxide, aluminum oxide and silica. The composition of the preferred reduced nickel-based catalyst is about 20 percent to about 30 percent nickel, about 20 percent to about 30 percent nickel (II) oxide, about 5 percent to about 15 percent aluminum oxide, and about 25 percent to about 37 percent silica, with percentages being by weight and totaling 100 percent. A particularly useful nickel-based catalyst is product number C46-7-03 RS, available from United Catalysts, Inc. (Louisville, Ky.). This nickel-based catalyst is available for purchase already reduced.

It is preferred that the starting materials be substantially free of materials which may reduce catalytic activity or completely inactivate either the copper-based or the nickel-based catalysts. It is also preferred that the copper-based catalyst and the nickel-based catalyst be kept at elevated temperatures to prevent physical damage to them caused by cooling, such as the deposition of materials into the pores of the catalyst support. Transfer of the copper-based catalyst and the nickel-based catalyst from the manufacturer's packaging into their respective reactor should be accomplished in a nitrogen-free and/or oxygen-free atmosphere, for example, by using a glove bag. After the completion of the vapor-phase hydrogenations, the reactors are preferably flushed with hydrogen for extended periods of time, which serves to sweep any remaining reactants, products or other materials away from the catalytic beds and maintain physical integrity of the copper-based catalyst and the nickel-based catalyst.

Although the literature reported the addition of poisons to lower the activity of a catalyst toward vapor-phase hydrogenations and to improve the conversion/yields of the desired product(s) or decrease the formation of undesirable product(s), it has been found that in the processes of the invention, the addition of poison had an insignificant effect on the product distribution or the conversion of the feedstock into the desired products.

The percent recovery of product from the first or second vapor-phase, catalytic hydrogenation was computed using the following equation:

$$\text{Percent Recovery} = \frac{\text{Product}}{\text{Furfural Flow Rate} \times \text{Maximum Mass Yields}} \times 100$$

where the product is defined as the sum of the solvent and aqueous layers and the maximum mass yields of the known components is used. The maximum mass yields listed in the table below were defined as the maximum amount of product per unit amount of substrate.

| Component | Maximum Mass Yield, (Y Max P/S) |
|---|---|
| 2-MF | 0.854 |
| 2-MTHF | 1.05 |
| Furfuryl Alcohol | 1.021 |

Various details of the invention may be changed without departing from its scope. Furthermore, the following non-limiting examples are provided for the purposes of illustration only of other features and advantages, the invention being defined by the claims.

EXAMPLES

The following examples are intended to further illustrate, without limiting, the processes of the invention.

Testing

Analysis of the furfural derivatives produced was performed by gas chromatography using an HP 5890 Series II chromatograph equipped with an HP 7673 injector (both available from Hewlett-Packard, Palo Alto, Calif.) and using System Gold software version 8.1 (available from Beckman Instruments, Inc., Fullerton, Calif.). Gas chromatography was performed on a two meter long column with an external diameter of 1/8" and packed with 5 percent Carbowax 2M 80/120 on Carboblack B (available from Restek, Bellefonte, Pa.). Furfural derivative samples were run through the column for five minutes at 70° C. and then the temperature was raised from 70° C. to 160° C., at 10° C. increments per minute, and finally the temperature was held steady for 10 minutes at 160° C.

Example 1

A vapor-phase, catalytic hydrogenation of furfural was conducted at atmospheric pressure using a vaporizer and reactor as described herein. The design of the vaporizer used for the vapor-phase, catalytic hydrogenation of furfural is shown in the schematic diagram as shown in FIG. 1.

The vaporizer had a vertical design with a feed line extending through the top of the vaporizer. The hydrogen gas was delivered through tubes extending through the top of the vaporizer. The temperature of the feed line was maintained by circulating heating oil inside coils positioned around the feed line within the vaporizer to improve the efficiency of vaporizing the feedstock. The feed line was placed to deliver the furfural-containing feedstock into the center of the vaporizer chamber. A thermowell near the bottom of the vaporizer contained a thermocouple used for temperature measurement. The lower portion of the vaporizer had a tapered design that reduced holdup inside the vaporizer and improved the combination of furfural-containing feedstock and hydrogen delivered into the reactor. The vaporizer was attached directly to the reactor using a compression fitting.

Figure 2:
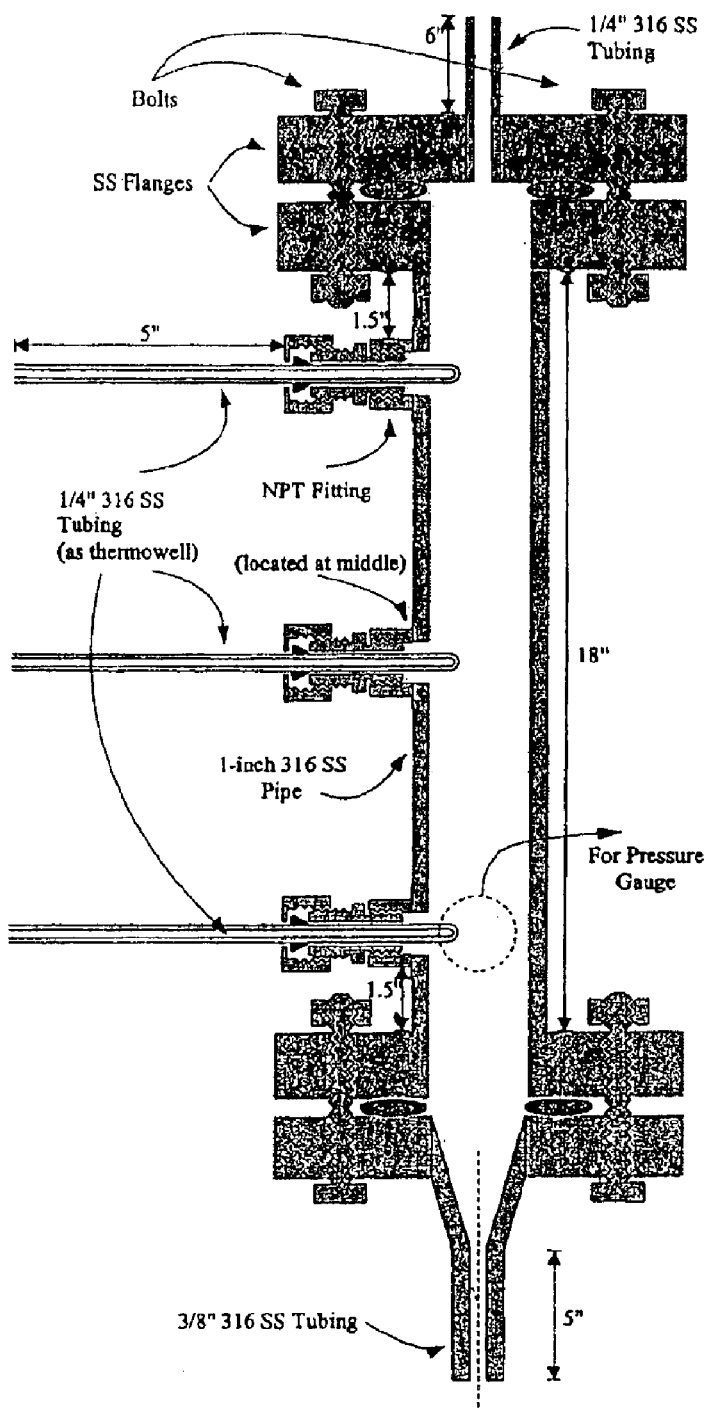
FIG. 2 is a schematic diagram illustrating the reactor used for the vapor-phase, catalytic hydrogenation of furfural in the present invention.

The reactor used for the vapor-phase, catalytic hydrogenation of furfural is shown in the schematic diagram in FIG. 2.

This reactor was made of one inch stainless steel pipe with three thermowells located at the top, middle and bottom sections of the reactor. The lower portion of the reactor also had a tapered design similar to that of the vaporizer, which reduced holdup inside the reactor. Heating tape was wrapped around the outside of the reactor and a thermocouple was inserted into the middle thermowell for temperature measurement.

A copper-based catalyst obtained from United Catalysts, Inc. (Louisville, Ky.) and identified as product number G-99B-0 was used for the vapor-phase hydrogenation. The surface area of the G-99B-0 catalyst was 30±10 square meters per gram. The table below identifies the chemical composition (as percent by weight) of the G-99B-0 catalyst, with percentages totaling 100 percent taking into account the small amounts (0.2 percent) of moisture may be bonded water in the actual metal oxide or catalyst matrix.

| Element | Compound | Composition |
|---|---|---|
| Copper | $CuO$ | 46.9 |
| Chromium | $Cr_2O_3$ | 46.0 |
| Barium | $BaCrO_4$ | 3.3 |
| Magnesium | $MnO_2$ | 3.6 |

Reduction of this copper-based catalyst was according to the manufacturer's directions and was accomplished within the hydrogenator prior to the vapor-phase hydrogenation of the furfural-containing feedstock. The furfural obtained from Great Lakes Chemical Corporation (Memphis, Tenn.) was vaporized and mixed with hydrogen within the vaporizer. The hydrogen was delivered into the vaporizer at a flow rate of about 2.0 ml/min throughout the reaction. Sufficient hydrogen was mixed in to provide about two moles of hydrogen per mole of furfural in the feedstock. The temperature within the vaporizer was maintained at about 180° C. The vaporized furfural-hydrogen mixture was fed into the hydrogenator at a flow rate of about 1.5 ml/min during the entire reaction so that sufficient residence time was achieved. The temperature of the hydrogenator was maintained at about 175° C. After about 15 minutes, the reaction reached a steady state, at which time 15-minute samples were collected every hour for five hours. All samples separated into two phases after standing at room temperature for a short time, namely an organic phase and an aqueous phase. The organic phase was analyzed using gas chromatography, as described above. There was no unreacted furfural present in the samples. The aqueous phase was not analyzed. The ratio of organic phase to aqueous phase remained fairly constant at about 80:20 throughout the reaction. As previously explained in detail, the maximum mass yields for the two components of the organic phase, namely 2-MF and FA, was used in the determination of the percent recovery, which was about 70 percent. Manipulation of the furfural flow rate revealed that the percent recovery increased as the furfural flow rate increased. For example, a percent recovery of about 82 percent was achieved at a flow rate of about 2.5 ml/min. The reaction produced an organic phase containing primarily 2-MF and FA with minor amounts of 2-pentanone and I-pentanol. The distribution of these compounds in the organic phase was as follows: about 85 percent for 2-MF, about 10 percent for FA and less than 3 percent for the other products.

Example 2

A vapor-phase, catalytic hydrogenation of 2-MF was conducted at atmospheric pressure using a vaporizer and reactor as described in Example 1. A nickel-based catalyst obtained from United Catalysts, Inc., Louisville, Ky. and identified as product number C46-07-3 RS was used for the vapor-phase hydrogenation. The C46-07-3 RS catalyst had a surface area of 138.2 square meters per gram, a pore volume of 0.5145 milliliters per gram and a compacted bulk density of 45.1 pounds per square foot. The weight-time for the vapor-phase, catalytic vapor-phase hydrogenation was determined to be $7.74 \times 10^4$ grams catalyst-minutes per liter. Weight-time was herein defined as the ratio of the mass of catalyst to the volumetric flow rate of the vaporized feedstock (for example, furfural or 2-methylfuran) mixed with hydrogen gas.

The 2-MF used was obtained from Great Lakes Chemical Corporation, Memphis, Tenn. It was vaporized and mixed with hydrogen within the vaporizer. The hydrogen was delivered into the vaporizer at a flow rate of about 2.0 ml/min throughout the reaction. Sufficient hydrogen was mixed in to provide about two moles of hydrogen per mole of 2-MF in the feedstock. The temperature within the vaporizer was maintained at about 180° C. The vaporized 2-MF-hydrogen mixture was fed into the hydrogenator at a flow rate of about 0.5 ml/min. The temperature of the hydrogenator was maintained at about 115° C. As in Example 1, after about 15 minutes, the reaction reached a steady state, at which time 15-minute samples were collected every hour for five hours. All samples separated into two phases after standing at room temperature for a short time, namely an organic phase and an aqueous phase. The organic phase was analyzed using gas chromatography, as described above. The aqueous phase was not analyzed. The reaction produced primarily 2-MTHF with small amounts of unreacted 2-MF and with minor amounts of 2-pentanone and 2-pentanol. The distribution of these compounds in the organic phase was as follows: greater than 75 percent for 2-MTHF, less than 15 percent for unreacted 2-MF and less than 1 percent of the other products.

Example 3

A vapor-phase, catalytic hydrogenation of 2-MF was conducted using the same set-up as described in Example 2 above, except that the hydrogenation temperature and 2-MF flow rate were modified. The reaction was conducted while maintaining the 2-MF flow rate at about 1.0 ml/min and varying the hydrogenation temperature from about 100° C. to about 130° C. These modified reaction conditions resulted in the percentage of 2-MTHF increasing to almost 90 percent and the percentage of unreacted 2-MF decreasing insignificant amounts (less than one percent).

Example 4

A vapor-phase, catalytic hydrogenation of furfural was conducted using the equipment set-up and process parameters described in Example 1 above to produce 2-MF. The concentration and percentage of the components of the reaction product is shown in the following table:

| Component | Concentration (grams per Liter) | Percentage |
| --- | --- | --- |
| 2-MF | 409.3 | 50.2 |
| MTHF | insignificant | 0 |
| 2-Pentanone | insignificant | 0 |
| 2-Pentanol | insignificant | 0 |
| 1-Pentanol | 22.7 | 2.8 |
| Unreacted Furfural | 36.9 | 4.5 |
| Furfuryl Alcohol | 293.4 | 36.0 |
| Other | 53.7 | 6.6 |

The 2-MF so produced was used in a vapor-phase, catalytic hydrogenation using the equipment set-up and process parameters described in Example 2 above. The reaction was conducted while maintaining the flow rate of the laboratory-prepared 2-MF at about 1.0 ml/min and the hydrogenation temperature at about 100° C. using a circulating oil bath. The reaction produced 2-MTHF, THFA, small amounts of unreacted 2-MF as well as minor amounts of 2-pentanone, 1-pentanol and 2-pentanol. The distribution of these products was as follows: about 45.5 percent 2-MTHF, about 22.8 percent THFA, about 11.3 percent 2-MF and about 10 percent or less of the other products. A comparison with data obtained from a reaction run under similar process conditions, but using 2-MF feedstock obtained from a commercial source (Great Lakes Chemical Corporation, Memphis, Tenn.) showed that a lower concentration of 2-MTHF was produced using the above-prepared, non-commercial 2-MF. This was likely due to the lower amount (50.2 percent) of 2-MF in the feedstock. The THFA obtained was the result of the vapor-phase hydrogenation of the 36.6 percent FA in the laboratory-prepared, non-commercial 2-MF feedstock. The amount of THFA would be substantially reduced by using a 2-MF feedstock free of FA, which can be done easily by separation of the FA from the 2-MF using simple distillation.

Example 5

A vapor-phase, catalytic hydrogenation of 2-MF was conducted using the equipment set-up described in Example 2 above to produce 2-MTHF, again using a hydrogenation temperature of 115° C., but adjusting the flow rate of 2-MF as described below and recycling the vapor stream exiting the reactor as described below. A refurbished HPLC pump Model 1330 was installed between the collection vessel and the reactor output. The reaction was started initially without recycling using a 2-MF flow rate of 1.5 ml/min for 30 minutes. Then, the recycling pump was turned on at 0.5 ml/min and the 2-MF flow rate decreased to 1.0 ml/min for the remaining 6 hours of the experiment. Fifteen minute samples were collected every hour. The concentration of unreacted 2-MF remained at less than 9 percent and the concentration of 2-MTHF exceeded 87 percent. The only minor product was 2-pentanol with a concentration of less than 4 percent. As a result of the recycling, the amount of unreacted 2-MF can be reduced.

Example 6

A continuous process for the two-stage vapor-phase, catalytic hydrogenation of furfural to 2-MTHF is conducted at atmospheric pressure using a vaporizer-reactor set-up similar to the one used in Example 1, but adding a second vaporizer-reactor set-up duplicating the first and connecting the two systems in series so that the vapor stream exiting the first reactor is directly delivered into the second vaporizer-reactor system.

A copper (cupric)-chrormite catalyst described in detail in Example 1 is used for the first vapor-phase hydrogenation. The furfural feedstock as described in detail in Example 1 is vaporized and mixed with hydrogen gas in the first vaporizer at a temperature of about 180° C. The furfural is mixed with sufficient hydrogen to provide about two moles of hydrogen per mole of furfural in the feedstock. The first vapor-phase hydrogenation occurs at a temperature of about 175° C. The first vaporous mixture exits the first hydrogenator and is mixed in a second vaporizer with sufficient hydrogen to provide about two moles of hydrogen per mole of 2-MF in the first vaporous mixture. The temperature of the second vapor-phase, catalytic hydrogenation is about 115° C. The second vapor-phase hydrogenation uses a nickel-based catalyst as described in detail in Example 1 above. A second vaporous mixture exits the second hydrogenator and is cooled, forming a liquid that separates into an aqueous phase and an organic phase. The desired product 2-MTHF is recovered from the organic phase.

Example 7

A two-stage vapor-phase, catalytic hydrogenation of furfural to 2-MTHF is conducted using an equipment set-up and process parameters as described in Example 6, except that the furfural-containing feedstock is derived from biomass. A biomass containing hemicellulose, derived from corn cobs and cleaned oat hulls is hydrolyzed to produce a xylose solution that is separated from a lignin residue by filtration. The xylose solution is then thermochemically processed to convert the xylose into furfural and water. The furfural is then concentrated by distillation and used directly as a furfural-containing feedstock in the two-stage vapor-phase, catalytic hydrogenation of furfural to 2-MTHF as described in detail in Example 6

What is claimed is:

1. A process for the preparation of furfural alcohol comprising the steps of:
   (a) vaporizing a furfural-containing feedstock;
   (b) mixing and hydrogenating the vaporized feedstock with sufficient hydrogen to provide about 2 moles of hydrogen per mole of furfural in the feedstock, the mixing and hydrogenating being carried out at a temperature at or above 175° C. in the presence of a reduced copper-based catalyst consisting essentially of cupric oxide, chromium (III) oxide, manganese oxide, and barium chromate to produce a first vaporous mixture of hydrogenated products including 2-methylfuran;
   (c) condensing the first vaporous mixture by directing the first vaporous mixture through one or more condensers and directing excess vapors through a plurality of traps prior to venting to the atmosphere;
   (d) allowing the condensate in the condensers to separate into an aqueous phase and an organic phase; and
   (e) recovering the furfural alcohol from the aqueous phase.

2. A process for the preparation of furfural alcohol comprising the steps of:
   (a) vaporizing a furfural-containing feedstock;
   (b) mixing and hydrogenating the vaporized feedstock with sufficient hydrogen to provide about 2 moles of hydrogen per-mole of furfural in the feedstock, the mixing and hydrogenating being carried out at a temperature of about 135° C. to about 150° C. in the presence of a reduced copper-based catalyst consisting essentially of cupric oxide, chromium (III) oxide, manganese oxide, and barium chromate to produce a first vaporous mixture of hydrogenated products including 2-methylfuran;
   (c) condensing the first vaporous mixture to form a condensate, and allowing said condensate to separate into an aqueous phase and an organic phase; and
   (d) recovering the furfural alcohol from said aqueous phase.

3. The process for the preparation of furfural alcohol of claim 2, wherein the condensing is by directing the first vaporous mixture through one or more condensers, and wherein excess vapors are directed through a plurality of traps prior to venting to the atmosphere.

4. A process for the preparation of tetrahydrofurfuryl alcohol comprising the steps of:
   (a) vaporizing a furfural-containing feedstock;
   (b) mixing and hydrogenating the vaporized feedstock with sufficient hydrogen to provide about 2 moles of hydrogen per mole of furfural in the feedstock, the mixing and hydrogenating being carried out at a temperature at or above 175° C. in the presence of a reduced copper-based catalyst consisting essentially of cupric oxide, chromium (III) oxide, manganese oxide, and barium chromate to produce a first vaporous mixture of hydrogenated products including 2-methylfuran;
   (c) mixing the first vaporous mixture with sufficient hydrogen to provide about 2 moles of hydrogen per mole of 2-methylfuran in the first vaporous mixture, the mixing and hydrogenating being carried out at a temperature of about 125° C. to about 155° C. in the presence of a reduced nickel-based catalyst consisting essentially of nickel, nickel (II) oxide, aluminum oxide, and silica to produce a second vaporous mixture of hydrogenated products including 2-methyltetrahydrofuran;

(d) condensing the second vaporous mixture to form a condensate, and allowing said condensate to separate into an aqueous phase and an organic phase; and (e) recovering the tetrahydrofurfuryl alcohol from said aqueous phase.

5. The process for the preparation of tetrahydrofurfuryl alcohol of claim 4, wherein the condensing is by directing the second vaporous mixture through one or more condensers, and wherein excess vapors are directed through a plurality of traps prior to venting to the atmosphere.

* * * * *